United States Patent

Muller et al.

[11] 3,972,707
[45] Aug. 3, 1976

[54] N-(PHENYLCARBAMOYL)-4-METHYLPIPERIDINE HERBICIDES COMPOSITIONS AND HERBICIDAL METHOD

[75] Inventors: Frank Muller, Siegertsbrunn; Norman Häberle; Peter Kinzel, both of Munich, all of Germany

[73] Assignee: Consortium fur Elektrochemische Industrie GmbH, Munich, Germany

[22] Filed: Mar. 27, 1975

[21] Appl. No.: 562,476

[30] Foreign Application Priority Data
Apr. 3, 1974  Germany.............................. 2416139

[52] U.S. Cl. ............................... 71/94; 260/293.77
[51] Int. Cl.$^2$ ............................................ A01N 9/22
[58] Field of Search.................... 260/293.77; 71/94

[56] References Cited
UNITED STATES PATENTS

| | | | |
|---|---|---|---|
| 3,787,393 | 1/1974 | Aya et al. | 260/293.77 |
| 3,823,006 | 7/1974 | Lorenz et al. | 71/94 |

FOREIGN PATENTS OR APPLICATIONS

| | | | |
|---|---|---|---|
| 2,053,333 | 5/1972 | Germany | 71/94 |
| 2,163,380 | 7/1972 | Germany | 71/94 |

OTHER PUBLICATIONS
Harada et al., Tetrahedron 26:1579–1588 (1970).

*Primary Examiner*—Sherman D. Winters
*Attorney, Agent, or Firm*—Hammond & Littell

[57] ABSTRACT

N-phenylcarbamoyl-4-methylpiperidine herbicides having the formula

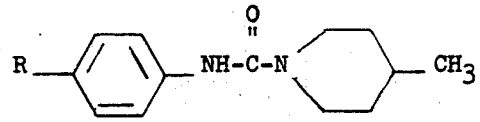

wherein R is a member selected from the group consisting of hydrogen and fluorine, compositions containing the same and the selective herbicidal method of use as a selective preemergence herbicide toward corn and a selective postemergence herbicide toward barley and, when R is H, toward corn.

9 Claims, No Drawings

N-(PHENYLCARBAMOYL)-4-METHYLPIPERIDINE HERBICIDES COMPOSITIONS AND HERBICIDAL METHOD

Various urea derivatives are useful as herbicides. N-phenyl-N',N'-dialkyl-urea (e.g. the N-3,4-dichlorophenyl compound), for example, have a herbicidal action, mainly with a low selectivity. N-(phenylcarbamoyl)-morpholine has also been described for use as a herbicide (U.S. Pat. No. 2,913,322), as have the urea derivatives of the general formula

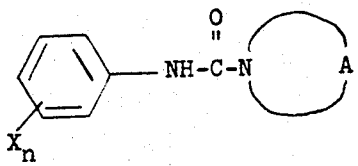

in which X denotes various substituents, but may be absent, and A denotes an alkylene group (German Offenlegungsschrift (DOS) No. 2,053,333). These latter substances show a selectivity toward sugarbeets, and one particular substance described as a selective sugarbeet herbicide is N-(phenylcarbamoyl)-piperidine, which has the formula

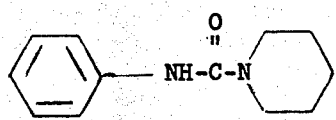

Further urea derivatives, useful as herbicides, are described in German Offenlegungsschrift (DOS) No. 2,163,380. These are of the general formula

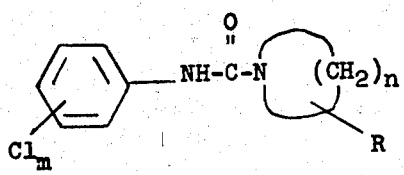

in which R denotes a hydrogen atom, or a lower alkyl group, m denotes 1 or 2, and n denotes 4, 5, or 6. These compounds exhibit selectivity toward various agricultural plants. One particular compound mentioned is N-(4'-chlorophenylcarbamoyl)-4-methyl-piperidine which has the formula

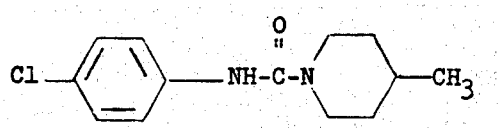

and this has a low toxicity toward rice plants.

An object of the present invention is the development of N-(phenylcarbamoyl)-4-methylpiperidine herbicides having the formula

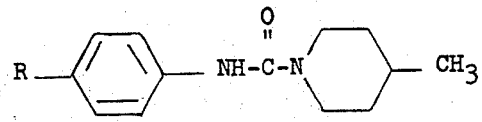

wherein R is a member selected from the group consisting of hydrogen and fluorine.

Another object of the present invention is the development of a herbicidal composition comprising an effective amount of at least one of the above herbicides and an inert carrier.

A further object of the present invention is the development of a method of combatting weeds both before and after emergence by applying at least one of the above herbicides.

These and other objects of the present invention will become more apparent as the description thereof proceeds.

It has now been found that certain other 1-phenylcarbamoyl-4-methyl-piperidines are useful as herbicides with an excellent selectivity, toward corn in particular, but also toward various other plants. According to the present invention N-phenylcarbamoyl-4-methyl-piperidine and N-(4'-fluorophenylcarbamoyl)-4-methylpiperidine are used as herbicides. These two compounds are novel compounds and can be represented by the general formula

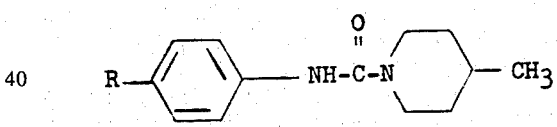

in which R denotes a hydrogen or fluorine atom. The first-mentioned compound (R being hydrogen) is preferred because of its better action and easier manufacture.

As will be apparent from the above, many similar compounds have been described as herbicides, but these two particular compounds have not hitherto been described. It was therefore surprising to find that they have a good herbicidal action, with an excellent selectivity toward corn. A further advantage of the present herbicides is their limited persistence in the soil (10 to 16 weeks), as compared with the long persistence (6 to 18 months) of 2-chloro-4-ethylamino-6-isopropylamino-s-triazine (known as atrazine), which is a commonly used selective herbicide towards corn. Another interesting characteristic of the present herbicides is that when used prior to emergence they spare only corn, whereas when applied after emergence they spare barley, and, when R is H, corn.

These two compounds are both solids at room temperature. The fluorine compound (R=F) melts at 137°C and the hydrogen compound (R=H) melts at 111° to 112°C. They can be prepared by known methods, for example, by either of the following two methods:

1)

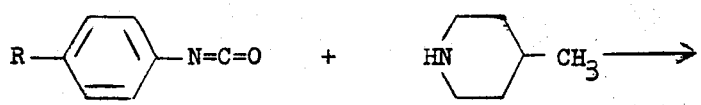

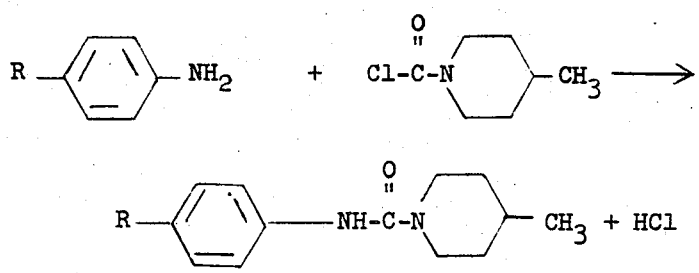

2)

The two herbicides according to the invention can be used per se. However, they are generally formulated according to conventional methods into herbicidal preparations to bring them into a form more suitable for being applied to the crops. These preparations can be in the form of, for example, emulsion concentrates, pastes, wettable powders, dusting agents, granulates, and solutions in organic solvents (e.g. acetone or toluene). They generally contain the active substance in an amount of from 0.1% to 95% by weight.

The emulsion concentrates, pastes, and wettable powders are suitably diluted with water prior to use to give herbicidal preparations in the form of spraying liquors suitable for application to the crop. Such spraying liquors generally contain the active substance in an amount of from 0.0001% to 5% by weight, preferably from 0.05% to 2.5% by weight. The herbicidal preparations are generally applied to the crops in amounts of from 1 to 9 kg, preferably from 2 to 6 kg, of active substance per hectare. The preparations can contain, as desired, other agriculturally useful chemicals, e.g. fertilizers and pesticides.

A suitable formulation for an emulsion concentrate is from 10% to 60% by weight of active substance; from 2% to 25% by weight of dispersants, e.g. sodium alkylbenzene sulfonates, calcium dodecylbenzene sulfonates, alkyl-polyoxyalkyleneglycol ethers, ethylene oxide condensation products with alkylphenols, and sodium alkylnaphthalene sulfonate; the remainder consisting of organic solvents, for example aromatic hydrocarbons (e.g. benzene, toluene, xylene, and aromatic naphtha), and aliphatic or cycloaliphatic solvents (e.g. ketones, such as acetone or cyclohexanone; alcohols, such as ethanol and isopropanol; ethers).

More particularly, a suitable formulation for an emulsion concentrate is: from 10 to 60% by weight of active substance; from 2 to 20% by weight of emulsifier (e.g. an alkylbenzene sulfonate and/or an alkyl-polyoxyalkylene glycol ether); from 0 to 50% by weight of an aromatic hydrocarbon solvent (e.g. xylene); and from 10 to 90% by weight of aliphatic or cycloaliphatic solvents (e.g. cyclohexanone or isopropanol).

Wettable powders suitably contain: from 10 to 80% by weight of active substance; from 20 to 80% by weight of inert fillers, e.g. kaolin, montmorillonite, China clay, magnesium carbonate, calcium carbonate, kieselguhr, highly dispersed silica, and fuller's earth; and a small amount of dispersant (e.g. those mentioned above).

More specifically, a suitable formulation for a wettable powder is: from 10 to 70% by weight of active substance; from 1 to 20% by weight of dispersants, e.g. lignin sulfonate or an alkyl-aryl sulfonate; and from 30 to 80% by weight of fillers, e.g. kaolin, China clay, fuller's earth.

Dusts generally contain from 5 to 25% by weight of active substance, with the remainder being inert fillers as already mentioned. Powder formulations of this type are generally prepared by mixing the various ingredients together, grinding the mixture to a particle size of 20 $\mu$ or less by means of a hammermill or other suitable grinding devices, mixing the formulation again, and finally sieving it.

The following examples are illustrative of the practice of the invention without being limitative in any respect.

EXAMPLES

Various tests have been carried out to illustrate the herbicidal action, particularly the selective herbicidal action, of the compounds used according to the invention and to compare it with the herbicidal action of two known herbicides of similar structure. The herbicides used were as follows:

A. N-phenylcarbamoyl-piperidine
(German Offenlegungsschrift No. 2,053,333)
B. N-(4'-chlorophenylcarbamoyl)-4-methyl-piperidine
(German Offenlegungsschrift No. 2,163,380)
C. N-(4'-fluorophenylcarbamoyl)-4-methyl-piperidine
D. N-phenylcarbamoyl-4-methyl-piperidine.

Each herbicide was used as an aqueous suspension of a wettable powder of the following formulation:
30% by weight of active substance
15% by weight of cellulose pitch
50% by weight of China clay 5% by weight of an alkyl-aryl sulfonate wetting agent, known under the trademark "Pernilac" of Pennsalt.

The herbicides were applied in amounts of 2, 4, and 6 kg of active substance per hectare. The pre-emergence action of the herbicides was tested by treating the soil with an aqueous suspension 24 hours after sowing. Their post-emergence action was tested by treating 14-day-old plants. In each case, the effect of the herbicides was evaluated 4 weeks after the treatment application. The results are listed in the Table below; 0 indicates that there was no damage to the plant, and 10 indicates that the plant was completely destroyed.

The superior action of the herbicides used according to the invention, as compared with the other herbicides is apparent from the results in the Table.

It should be noted that the effectiveness of the herbicides according to the invention is not restricted to the weeds mentioned in the tests. They are, in general, active against unicotyledonous varieties, for example, agrostic, pea, finger grass, bird weed, pile grass, various types of millet (e.g. finger millet), and crab grass, as well as against dicotyledonous varieties, for example, chick weed, pig weed, veronica, camomile, French weed, urtica, and silver weed.

however, that other expedients known to those skilled in the art or disclosed herein may be employed without departing from the spirit of the invention or the scope of the appended claims.

We claim:

1. An N-phenylcarbamoyl-4-methylpiperidine herbicide having the formula

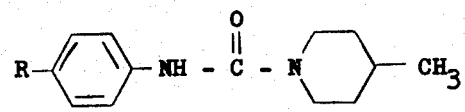

wherein R is a member selected from the group consisting of hydrogen and fluorine.

2. The compound of claim 1 wherein R is hydrogen.
3. The compound of claim 1 wherein R is fluorine.
4. A herbicidal composition comprising a herbicidally effective amount of a compound of claim 1 and an inert carrier.
5. A method of combatting weeds comprising applying to the soil before emergence of weeds a herbicidally effective amount of a compound of claim 1.
6. A method of combatting weeds comprising contacting weeds with a herbicidally effective amount of a

TABLE

| Herbicide | kg/ha | summer barley | mustard | sugar beet | wild oats | cleavers | corn flower | corn |
|---|---|---|---|---|---|---|---|---|
| Pre-emergence | | | | | | | | |
| A | 2 | 3 | 8 | 2 | 4 | 0 | 6 | 0 |
| A | 4 | 6 | 10 | 4 | 7 | 1 | 10 | 2 |
| A | 6 | 7 | 10 | 6 | 7 | 3 | 10 | 1 |
| B | 2 | 0 | 3 | 5 | 0 | 0 | 2 | 0 |
| B | 4 | 0 | 7 | 8 | 2 | 1 | 4 | 0 |
| B | 6 | 0 | 9 | 9 | 5 | 4 | 7 | 1 |
| C | 2 | 6 | 10 | 10 | 8 | 7 | 10 | 1 |
| C | 4 | 7 | 10 | 10 | 9 | 9 | 10 | 2 |
| C | 6 | 8 | 10 | 10 | 10 | 9 | 10 | 2 |
| D | 2 | 8 | 10 | 10 | 10 | 8 | 8 | 1 |
| D | 4 | 8 | 10 | 10 | 9 | 8 | 10 | 1 |
| D | 6 | 8 | 10 | 10 | 10 | 9 | 10 | 2 |
| Post-emergence | | | | | | | | |
| A | 2 | 0 | 1 | 0 | 0 | 0 | 0 | 0 |
| A | 4 | 0 | 2 | 2 | 0 | 0 | 0 | 0 |
| A | 6 | 0 | 3 | 3 | 0 | 2 | 1 | 0 |
| B | 2 | 1 | 7 | 5 | 3 | 5 | 7 | 5 |
| B | 4 | 4 | 8 | 7 | 5 | 5 | 8 | 9 |
| B | 6 | 6 | 8 | 8 | 6 | 5 | 8 | 10 |
| C | 2 | 1 | 8 | 8 | 4 | 7 | 8 | 7 |
| C | 4 | 3 | 8 | 8 | 6 | 7 | 9 | 6 |
| C | 6 | 5 | 9 | 8 | 7 | 7 | 9 | 8 |
| D | 2 | 0 | 10 | 6 | 5 | 8 | 8 | 1 |
| D | 4 | 1 | 9 | 6 | 6 | 8 | 10 | 2 |
| D | 6 | 1 | 10 | 10 | 10 | 8 | 10 | 1 |

These results clearly demonstrate the unexpected pre-emergence selective herbicidal action towards corn of both compounds, as compared with the prior art compounds which had a broader spectrum of action. The post-emergence selective herbicidal action towards barley of both compounds, as well as that of N-phenylcarbamoyl-4-methyl-piperidine towards corn, is likewise demonstrated.

The preceding specific embodiments are illustrative of the practice of the invention. It is to be understood, compound of claim 1.

7. A method of selectively killing weeds in fields of corn comprising applying to the said fields a herbicidally effective amount of N-phenylcarbamoyl-4-methyl-piperidine.
8. The method of claim 7 wherein the compound is applied pre-emergence.
9. The method of claim 7 wherein the compound is applied post-emergence.

* * * * *